US008809585B2

(12) United States Patent
Riedner et al.

(10) Patent No.: US 8,809,585 B2
(45) Date of Patent: Aug. 19, 2014

(54) SYNTHESIS SCHEME FOR LACOSAMIDE

(75) Inventors: Jens Riedner, Ennis (IE); Gavin Dunne, Toomevara (IE)

(73) Assignee: UCB Pharma GmbH, Monheim (DE)

( * ) Notice: Subject to any disclaimer, the term of this patent is extended or adjusted under 35 U.S.C. 154(b) by 647 days.

(21) Appl. No.: 12/961,705

(22) Filed: Dec. 7, 2010

(65) Prior Publication Data

US 2011/0130350 A1 Jun. 2, 2011

Related U.S. Application Data

(62) Division of application No. 11/664,316, filed as application No. PCT/EP2005/010603 on Sep. 30, 2005, now Pat. No. 7,884,134.

(30) Foreign Application Priority Data

Oct. 2, 2004 (EP) ..................... 04023556

(51) Int. Cl.
*C07C 231/02* (2006.01)
(52) U.S. Cl.
USPC ......................................... 564/136
(58) Field of Classification Search
CPC ............................. C07C 233/18; A61K 31/16
See application file for complete search history.

(56) References Cited

U.S. PATENT DOCUMENTS

| 5,585,358 | A | 12/1996 | Bialer et al. ................. 514/19 |
| 6,048,899 | A | 4/2000 | Kohn et al. ................. 514/626 |
| 6,803,481 | B2 | 10/2004 | Selve .......................... 560/157 |
| 7,416,864 | B2 | 8/2008 | Stoehr ........................ 435/106 |
| 7,427,601 | B2 | 9/2008 | Stoehr .......................... 514/19 |
| 7,687,553 | B2 | 3/2010 | Beyreuther et al. ............ 514/7 |
| 7,718,161 | B2 | 5/2010 | Stoehr ........................ 514/563 |
| 7,794,987 | B2 | 9/2010 | Stoehr .......................... 514/19 |
| 7,820,857 | B2 | 10/2010 | Stoehr et al. .................. 514/19 |
| 7,875,652 | B2 | 1/2011 | Selve .......................... 515/616 |
| 7,884,134 | B2 | 2/2011 | Riedner et al. ................ 514/561 |
| 8,008,351 | B2 | 8/2011 | Scheller et al. .............. 514/616 |
| 8,053,476 | B2 | 11/2011 | Selve .......................... 514/575 |
| 2002/0052418 | A1 | 5/2002 | Shirvan et al. ............... 514/626 |
| 2004/0204495 | A1 | 10/2004 | Shirvan et al. ............... 514/616 |
| 2005/0085423 | A1 | 4/2005 | Selve ............................ 514/17 |
| 2005/0277596 | A1 | 12/2005 | Stohr ............................ 514/19 |
| 2006/0009384 | A1 | 1/2006 | Rudd et al. .................... 514/12 |
| 2006/0100157 | A1 | 5/2006 | Rauschkolb-Loffler et al. ............................... 514/18 |
| 2006/0252749 | A1 | 11/2006 | Stohr ............................ 514/220 |
| 2007/0042969 | A1 | 2/2007 | Rauschkolb-Loffler et al. ............................... 514/19 |
| 2007/0043120 | A1 | 2/2007 | Beyreuther et al. ........... 514/616 |
| 2007/0048372 | A1 | 3/2007 | Beyreuther et al. ........... 424/464 |
| 2007/0197657 | A1 | 8/2007 | Beyreuther et al. ........... 514/616 |
| 2008/0280835 | A1 | 11/2008 | Beyreuther et al. .............. 514/2 |
| 2009/0018197 | A1 | 1/2009 | Rudd et al. .................... 514/563 |
| 2009/0241205 | A1 | 9/2009 | Beyreuther et al. .............. 800/9 |
| 2010/0029543 | A1 | 2/2010 | Beyreuther et al. .............. 514/2 |
| 2010/0099770 | A1 | 4/2010 | Selve .......................... 514/616 |
| 2010/0240576 | A1 | 9/2010 | Stoehr ......................... 514/17.7 |
| 2010/0256179 | A1 | 10/2010 | Stöhr et al. .................... 514/327 |
| 2010/0256241 | A1 | 10/2010 | Stoehr et al. .................. 562/553 |
| 2010/0260716 | A1 | 10/2010 | Stöhr et al. .................. 424/85.6 |
| 2010/0273714 | A1 | 10/2010 | Stoehr ......................... 514/17.7 |
| 2010/0324144 | A1 | 12/2010 | Heers et al. .................. 514/248 |
| 2011/0082211 | A1 | 4/2011 | Selve .......................... 514/370 |
| 2012/0225119 | A1 | 9/2012 | Beyreuther et al. ........... 424/456 |
| 2012/0238614 | A1 | 9/2012 | Stöhr .......................... 514/424 |
| 2013/0251803 | A1 | 9/2013 | Cawello et al. |
| 2013/0251813 | A1 | 9/2013 | Cawello et al. |
| 2014/0066515 | A1 | 3/2014 | Heers et al. |

FOREIGN PATENT DOCUMENTS

| JP | S51-029456 | 3/1976 | ............ C07C 125/06 |
| JP | 62-132849 | 6/1987 | ............ C07C 125/06 |
| JP | 11-029544 | 2/1999 | ............ C07D 207/16 |
| WO | WO 97/33861 | 9/1997 | ............ C07C 237/22 |
| WO | WO 2004/014895 | 2/2004 | ............ C07D 403/04 |

OTHER PUBLICATIONS

Greene, Protective Groups in Organic Chemistry, 1981, John Wiley & Sons, Inc., New York, pp. 232, 233, 239 and 240.*
Andurkar, et al. (1998) "Synthesis and anticonvulsant activities of (R)-(O)-methylserine derivatives." Tetrahedron: Asymmetry 9(21): 3841-3854.
Barlos, et al. (1983) "Convenient synthesis of N-trityl-O-alkyl-L-hydroxyamino acids and derivatives. Application to the synthesis of related peptides." Tetrahedron 39(3): 475-478.
Bialer, et al. (2001) "Progress report on new antiepileptic drugs: a summary of the Fifth Eilat Conference (Eilat V)." Epilepsy Res. 43:11-58.
Bialer, et al. (2002) "Progress report on new antiepileptic drugs: a summary of the Sixth Eilat Conference (Eilat VI)." Epilepsy Res. 51:31-71.
Carey, et al. (2001) Advanced Organic Chemistry, Part B, 4th Ed. Kluwer Academic/Plenum Publishers, New York, 172-179.
Chen, et al. (1979) "Simple preparations of N-(tert-butyloxycarbonyl)-O-methyl-L-serine and N-(tert-butyloxycarbonyl)-O-methyl-L-threonine by direct methylation." J. Org. Chem. 44(13): 2299-3000.
Fisher, et al. (2003) "Trigeminal Neuralgia: current treatments and future developments." Expert Opin. Emerging Drugs 8(1):123-143.
Hovinga (2002) "Novel anticonvulsant medications in development." Expert Opin. Investig. Drugs 11(10) 1387-1406.
McKillop et al. (1974) "The use of phase-transfer catalysis for the synthesis of phenol ethers" Tetrahedron 30: 1379-1382.
Mederski, et al. (2004) "Chlorothiophenecarboxamides as P1 surrogates of inhibitors of blood coagulation factor Xa." J. BMCL. 14(23): 5817-5822.

(Continued)

*Primary Examiner* — Paul A Zucker
(74) *Attorney, Agent, or Firm* — Harness, Dickey & Pierce, P.L.C.

(57) ABSTRACT

The present invention is concerned with an improved method of producing (R)-2-acetamido-N-benzyl-3-methoxypropionamide (lacosamide) comprising the 0-methylation of a compound of formula (I) to produce a compound of formula (II) in a single step reaction.

15 Claims, 1 Drawing Sheet

(56) References Cited

OTHER PUBLICATIONS

Nobeshima (1999) "Preparation of N-alkoxycarbonylated, N-alkenyloxycarbonylated, and N-arylalkoxycarbonylated amino acids or peptides." Database CA 'Online!, Chemical Abstracts Service retrieved from STN Database accession No. 1999:78500 abstract.

Varga, et al. (1985) "Ring-formation by methylation of phenylserine derivatives" ACH 120(4):247-249.

Wolff, et al.(2000) "Uses of quaternary phosphonium compounds in phase transfer catalysis" Chemistry Today January/February: 29-32.

International Search Report for PCT/EP2005/010603 dated Jul. 15, 2004.

Office Action, dated Jun. 29, 2010 issued in U.S. Appl. No. 11/664,316.

Office Action dated May 19, 2010 issued in U.S. Appl. No. 11/664,316.

International Preliminary Report on Patentability dated Apr. 3, 2007 issued in PCT Application No. PCT/EP2005/010603.

Yadav, G.D. et al. Selective O-Alkylation of 2-Naphthol using Phosphonium-Based Ionic Liquid as the Phase Transfer Catalyst, *Organic Process Research & Development*, vol. 14, (2010), pp. 722-727.

* cited by examiner

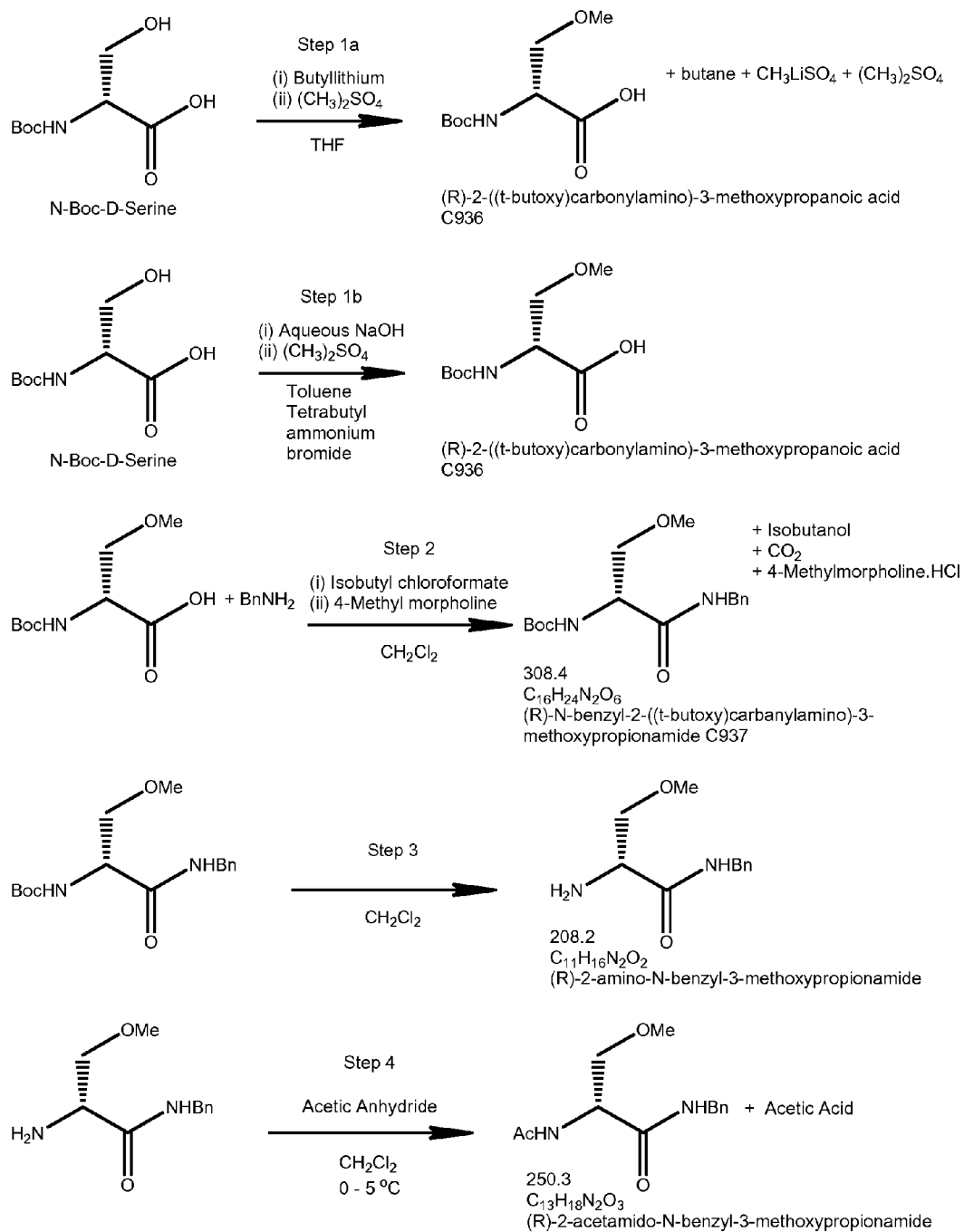

SYNTHESIS SCHEME FOR LACOSAMIDE

PRIORITY CLAIM TO RELATED PATENT APPLICATIONS

This application is a divisional application of Ser. No. 11/664,316, filed Sep. 28, 2007, now U.S. Pat. No. 7,884,134, issued 8 Feb. 2011, which is a national stage of International Patent Application No. PCT/EP2005/010603, filed 30 Sep. 2005, which claims priority to EP 04023556.6, filed 2 Oct. 2004. The above referenced applications are incorporated herein by reference in their entirety.

BRIEF DESCRIPTION OF THE DRAWING

FIG. 1 shows the improved synthesis scheme involved in the production of Lacosamide. Progressively, the chemical steps produce (R)-2-N-Boc-amino-3-methoxypropanoic acid (C-936) using butyllithium (Step 1a) or PTC (Step 1b), a methylene chloride solution of (R)—N-benzyl-2-N-Boc-amino-3-methoxypropionamide (C-937) (Step 2), a methylene chloride solution of (R)-2-amino-N-benzyl-3-methoxypropionamide (Step 3), and finally, Lacosamide (Step 4).

DETAILED DESCRIPTION (R)-2-acetamido-N-benzyl-3-methoxypropionamide (recommended INN: lacosamide) is an anticonvulsant drug useful for treating epilepsy and pain. Two methods for producing this compound are disclosed in U.S. Pat. No. 6,048,899.

Scheme 2 of U.S. Pat. No. 6,048,899 comprises the benzylamide formation prior to the O-methylation. However, this reaction scheme results in various impurities which must be removed by chromatography which is impractical on an industrial scale. Also, the yield of the individual steps is only between 80 and 85%.

Scheme 1 of U.S. Pat. No. 6,048,899 involves the O-methylation of an N-protected D-serine prior to benzylamide formation, N-deprotection and N-acetylation. Although this production scheme is a more promising starting point for upscaling it suffers from major deficiencies. Most importantly, the O-methylation of N-protected D-serine using silver (I) oxide and methyliodide is impractical and expensive and results in partial racemisation (about 15%) which reduces the yield of this step to 79%. Also, the removal of the S-enantiomer during production of (R)-2-acetamido-N-benzyl-3-methoxypropionamide is extremely difficult.

It has now been detected, surprisingly, that the racemisation can be avoided by using alternative O-methylation methods, such as e.g. O-methylation using phase transfer catalysis or O-methylation using organolithium and a suitable methylation agent, such as dimethyl sulfate.

Also, the present invention provides an improved lacosamide synthesis route, wherein the O-methylation method is selective for the alcoholic hydroxy group of the N-protected D-serine. Accordingly, compared to the unspecific methylation suggested in scheme 1 of U.S. Pat. No. 6,048,899, which also leads to the esterification of the carboxylic group, the present invention results in a shortened, more effective synthesis, wherein the subsequent step of hydrolysing the methyl ester group of an intermediate is avoided.

Accordingly, the present invention relates to an improved method of producing (R)-2-acetamido-N-benzyl-3-methoxypropionamide comprising the O-methylation of a compound of formula I

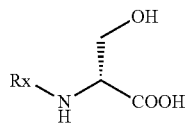

formula I to produce a compound of formula II

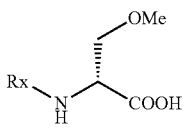

formula II wherein Rx is an N-protecting group, characterised in that the O-methylation is being carried out in a one-step reaction and wherein racemisation is avoided such that the compound of formula II is obtained as an R-enantiomer of at least 88%, preferably at least 90% and even more preferred of at least 95, 96, 97, 98 or 99% enantiomeric purity.

The language "one-step reaction" as used in this patent application means that when transforming a compound of formula I to a compound of formula II no significant amount (i.e. an amount of 5 Mol % or more) of ester of the carboxyl group is formed that needs to be hydrolysed in a separate step. Usually, even less than 1 Mol % of ester is formed which is then removed during the further processing to lacosamide as described further below without the need for any additional hydrolysis step.

The inventive O-methylation can be achieved by adding to a compound of formula I, such as e.g. to N-Boc-D-serine, a methylation agent in the presence of an organo metal compound, preferably an organo lithium compound. Suitable methylation agents are e.g. dimethyl sulphate, trimethyl phosphate or methyl iodide with dimethyl sulphate being particularly preferred. The organo lithium compound is preferably an alkyl lithium compound, such as butyllithium, methyllithium or hexyllithium or an aryllithium compound, such as phenyl lithium. More preferably the organo lithium compound is t-butyllithium or n-butyllithium and particularly preferred n-butyllithium. Alternatively, other organo metal compounds comprising a metal-carbon binding may be used, such as organo zinc compounds including organo zinc halides, organo aluminium compounds including organo aluminium halides, organo tin compounds including organo tin halides or/and organo magnesium compounds including organo magnesium halides (Grignard compounds), wherein halides include Cl, Br or/and I. The organo moiety may be aryl or alkyl. Preferred are Grignard compounds Alkyl-Mg—Y, or Aryl-Mg—Y, wherein Y is Cl, Br or I. THF/2-methoxyethyl ether mixtures, diethoxymethane or, preferably, THF may be used as solvent. The reaction is usually allowed to proceed for at least 5 hours at 0-10 C, and preferably for 7-24 hours at 0-10° C., most preferably for 9-18 hours at 0-5° C. Also, the reaction may be performed at higher or lower temperatures such as any temperature between −10 and +25° C. if the reaction time is adapted accordingly.

If the N-protecting group Rx of the compound of formula I is N-Boc a typical reaction can be illustrated by the following scheme (step 1-A)

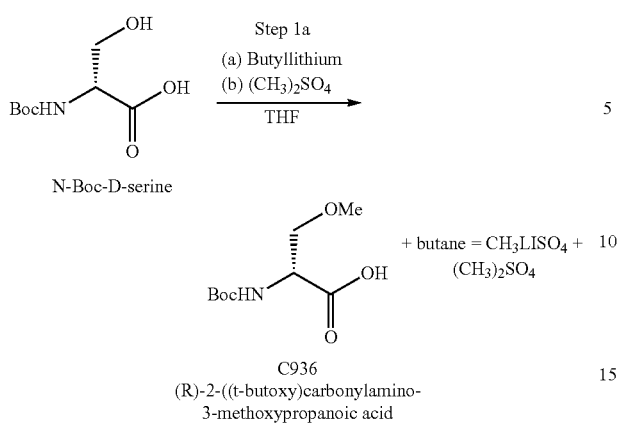

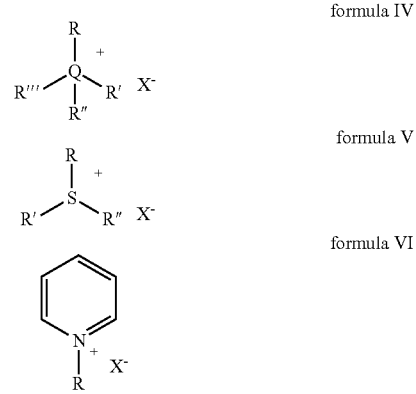

Surprisingly, this process does not result in methyl ester formation or significant racemisation of the product. The experimental yield is 91%, with the major impurities being N-methylations (e.g. Example 1). Therefore, the yield of the methylation according to the method of the present invention using an organo metal compound may be at least 85%, preferably at least 90%.

Typically the amount of ester impurity after methylation using an organo metal or preferably an organo lithium compound, in particular after step 1a is significantly below 1 Mol %, preferably below 0.1 Mol % and is regularly below the limit of detection.

In an alternative route the selective O-methylation of the alcoholic group of N-protected D-serine is performed by phase transfer catalysis ("PTC"). PTC is a method that makes use of heterogeneous two-phase systems—one phase being an aqueous or solid phase and a reservoir of reacting anions or a base for the generation of organic anions, whereas the organic reactants and catalysts are located in the second, organic phase.

Usually, a quarternary ammonium, phosphonium or sulfonium salt, such as e.g. a tetraalkylammonium halide, is used as phase transfer catalyst. Suitable catalysts and PTC reagents can be purchased from many vendors, e.g. from Sigma-Aldrich or Hawks Chemical.

Accordingly, one embodiment of the present invention relates to a method of producing lacosamide, characterized in that a compound of formula I is O-methylated to a compound of formula II by performing the reaction as a phase transfer catalysis.

Typically this method comprises the addition of a methylation reagent, such as dimethylsulfate, methyl iodide or trimethyl phosphate to a phase transfer reaction system comprising the compound of formula I, an aqueous phase, an organic phase and a phase transfer catalyst.

In the PTC of the present invention preferably (a) the methylation agent is selected from dimethylsulfate, methyl iodide or trimethyl phosphate, wherein dimethylsulfate is particularly preferred;

(b) the first (aqueous) phase is an alkaline aqueous solution, such as aqueous sodium hydroxide, aqueous lithium hydroxide, aqueous potassium hydroxide, aqueous sodium carbonate or aqueous potassium carbonate, wherein aqueous sodium hydroxide is particularly preferred;

(c) the second (organic) phase is selected from toluene, hexane, methylene chloride or methyl t-butyl ether, with toluene being particularly preferred; and (d) the phase transfer catalyst is an ammonium or phosphonium salt of formula IV, a sulfonium salt of formula V or a pyridinium salt of formula VI wherein R, R', R" and R'" are independently selectable alkyl, aryl or aralkyl groups, Q is a nitrogen or phosphorus and X is a halide, acetate, p-toluenesulfonate, trifluoromethanesulfonate, hexafluoroantimonate, hydroxide, perchlorate, hydrogensulfate, thiocyanate or tetrafluoroborate.

Examples of suitable phase transfer catalysts are tetraethylammonium p-toluenesulfonate, tetrapropylammonium trifluoromethanesulfonate, tetraphenylphosphonium hexafluoroantimonate, cetylpyridinium bromide, triphenylmethyl triphenylphosphonium chloride, benzyltriethylammonium chloride, benzyltrimethylammonium chloride, benzyltriphenylphosphonium chloride, benzylributylammonium chloride, butyltriethylammonium bromide, butyltriphenylphosphonium bromide, cetyltrimethyl ammonium bromide, cetyltrimethyl ammonium chloride, ethyltriphenylphosphonium bromide, ethyltriphenylphosphonium iodide, methyltrioctylammonium bromide, methyltriphenylphosphonium bromide, methyltriphenylphosphonium iodide, phenyltrimethylammonium chloride, tetrabutylammonium hydroxide, tetrabutylammonium perchlorate, tetrabutylammonium bromide, tetrabutylammonium hydrogensulphate, tetrabutylammonium iodide, tetrabutylammonium tetrafluoroborate, tetrabutylammonium thiocyanate, tetraethylammonium hydroxide, tetraethylammonium iodide, tetraethylammonium bromide, tetramethylammonium chloride, tetramethylammonium iodide, tetramethylammonium chloride, tetraoctylammonium bromide, tetraphenylphosphonium bromide, tetrapropylammonium hydroxide, tetrapropylammonium bromide and tributylmethylammonium chloride, wherein tetrabutylammonium salts and particularly tetrabutylammonium halides, e.g. the bromide are especially preferred.

In the PTC of the present invention suitable concentrations of components (a)-(d) as defined above are as follows (a) the amount of methylation agent is 1 to 5 molar equivalents with respect to the compound of formula I (b) aqueous alkali is provided as a 5 to 50% w/w solution and in an amount of 1.1 to 10 molar equivalents with respect to the compound of formula I (c) the amount of organic solvent with respect to the compound of formula I is preferably between 3-20 volumes, in particular 3-20 l/kg compound of formula I (d) the amount of phase transfer catalyst is between 0.01 to 0.1 molar equivalents of the compound of formula I In the present invention, in particular in formula IV to VI "aryl" refers to an aromatic group, substituted with one or more substituents or unsubstituted, which contains from 6 up to 18 ring carbon atoms and up to a total of 25 carbon atoms and includes polynuclear aromatics. These aryl groups may be monocyclic, bicyclic, tricyclic or polycyclic and may be fused rings. A polynuclear aromatic compound as used herein, is meant to encompass bicyclic fused aromatic ring systems containing from 10-18 ring carbon atoms and up to a total of 25 carbon atoms. In the aryl group, one to six carbon atoms may be replaced by a heteroatom, such as oxygen, sulfur or/and nitrogen. "Aryl" comprises unsubstituted phenyl; unsubstituted naphtyl; phenyl or napthyl substituted with one or more substituents selected from e.g. hydroxy, carboxy, halogen, nitro, C1-6 alkyl, C1-6 alkoxy, amino; substituted or unsubstituted heteroaryls such as pyrroyl; thienyl, indolyl, etc. In the present invention, in particular in formula IV, "aryl" is preferably chosen from unsubstituted phenyl or substituted phenyl, e.g. 2,6-difluorophenyl, p-nitrophenyl or p-toluoyl. Unsubstituted phenyl is particularly preferred.

In the present invention, in particular in formula IV to VI "alkyl" comprises branched or linear saturated hydrocarbon chains. Preferably "alkyl" is a branched or linear hydrocarbon with up to 20 carbon atoms, more preferably with up to 6 carbon atoms; most preferably with up to 4 carbon atoms. The hydrocarbon may be substituted with one or more substituents or unsubstituted. Preferred examples of "alkyl" are cetyl, octyl, heptyl, pentyl, butyl, propyl, ethyl and methyl.

In the present invention, in particular in formula IV to VI, "aralkyl" means a group aryl-alkyl wherein "aryl" and "alkyl" are as defined above. Preferably "aralkyl" is benzyl.

In the present invention, substitution refers to substitution of a H atom by e.g. hydroxy, carboxy, halogen, nitro, C1-6 alkyl, C1-6 alkoxy, amino.

The PTC reaction is usually allowed to proceed at 0-10° C. for at least 30 minutes, e.g. for 0.5 to 24 hours, preferably for at least 45 minutes and even more preferred for at least 1 hour. The PTC of the present invention under the specific condition of e.g. Example 2 (step 1-B) yielded 96%. The yield of the PTC of the present invention may thus be at least 85%, preferably at least 90%, even more preferably at least 91%, 92%, 93%, 94%, 95% or 96%.

A compound of formula I is obtainable from many vendors e.g. from Sigma-Aldrich or Lancaster. N-Boc-D-serine can also be produced by reacting D-serine with di-t-butyl dicarbonate to N-Boc-D-serine in a phase transfer catalysis reaction using essentially the conditions (e.g. choice and concentration/amount of alkali, solvent, PCT-catalysts, temperature, reaction time etc) as described above, except that di-t-butyl dicarbonate is used as the reagent instead of a methylation agent.

If the N-protecting group of the compound of formula I is Boc (t-Butoxycarbonyl), a preferred PTC reaction can be illustrated by the following scheme (Step 1-B)

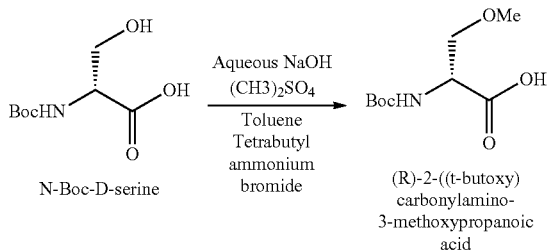 [SMILES: CC(C)(C)OC(=O)N[C@H](CO)C(=O)O ; COC[C@@H](NC(=O)OC(C)(C)C)C(=O)O]

This reaction does not result in any racemisation or esterification of the product. Also, the yield is further improved with impurity levels of only about 1%.

Typically the amount of ester impurity after methylation by PTC, in particular after step 1-B is well below 1 Mol %, preferably below 0.1 Mol %, and usually below the limit of detection.

The process of the current invention may further comprise the step of processing the compound of formula II to a compound of formula III (Step 2)

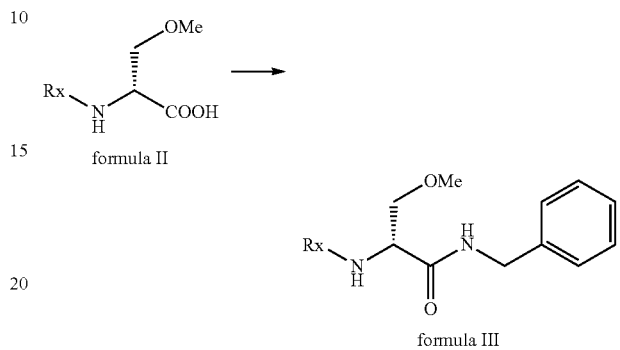

The benzyl amide formation can be performed by adding to a compound of formula II an amount of benzylamine in the presence of (a) a base such as triethylamine, diisopropylethylamine, 1,8-diazabicyclo [5.4.0]undec-7-ene, potassium bicarbonate or a morpholine derivative, preferably 4-methylmorpholine and (b) an activator of the carboxyl group such as a carbodiimide or an alkyl chloroformate, preferably isobutyl chloroformate.

Experimentally, the yield of the benzylamid formation under the conditions of e.g. Example 3 (step 2) was typically between 90% and 99%. Thus, the yield of the benzylamid formation of the present invention may be in the range of at least 85% up to 99.9%, preferably in the range of at least 90% up to 99% product.

This step 2 has been basically described in U.S. Pat. No. 6,048,899, which is included herein by reference.

Suitable protecting groups in the method according to the present invention are e.g. t-butoxycarbonyl (Boc) or carbobenzoxy (Cbz), with the Boc group being particularly preferred.

In the compound of formula III the protecting group Rx can be cleaved off to obtain (R)-2-amino-N-benzyl-3-methoxypropionamide by appropriate measures known from the art. For example, if the protecting group Rx is a carbobenzoxy group it may be cleaved off with H2, Pd/C as described in U.S. Pat. No. 6,048,899. If the protecting group is a Boc group this group may be conveniently removed with an acid, such as hydrochloric acid, e.g. at room temperature (step 3).

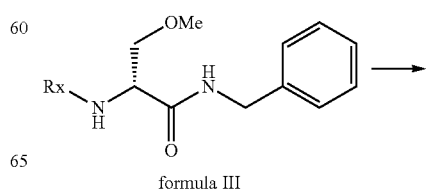

-continued

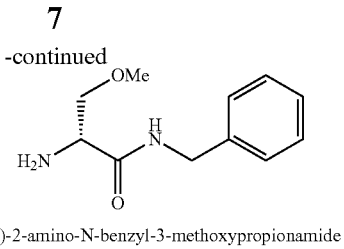

(R)-2-amino-N-benzyl-3-methoxypropionamide

Experimentally, the amine formation under the conditions of e.g. Example 3, step 3 typically yielded product in an amount ranging from 95% to 100%. Thus, the amine formation step in the method of the present invention may yield at least 85%, preferably at least 90%, more preferably at least 95% product.

(R)-2-amino-N-benzyl-3-methoxypropionamide can then be transformed to lacosamide by N-acetylation using acetic anhydride (step 4)

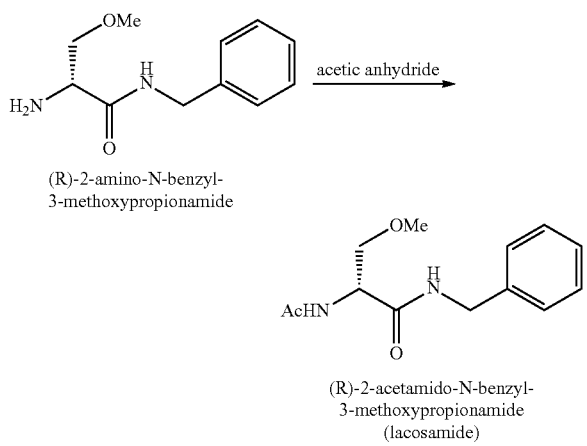

(R)-2-amino-N-benzyl-3-methoxypropionamide (R)-2-acetamido-N-benzyl-3-methoxypropionamide (lacosamide)

Experimentally, the acetylation under the conditions of e.g. Example 3, step 4 typically yielded between 81% and 95%. The yield of the acetylation step in the method of the present invention may thus be in the range of at least 70% up to 99%, preferably in the range of at least 80% up to 95%.

This step has been also described in U.S. Pat. No. 6,048,899. However, U.S. Pat. No. 6,048,899 suggests the use of acetic anhydride in the presence of a base, e.g. pyridine. It has now been found unexpectedly that the pure (R)-enantiomer can be also obtained effectively if the toxic pyridine is removed from the reaction mixture.

One embodiment of the present invention is thus the production of lacosamide comprising a step of N-acetylation of (R)-2-amino-N-benzyl-3-methoxypropionamide with acetic anhydride in the absence of a base, in particular in the absence of pyridine. The advantage of a base-free reaction is that toxic bases, such as pyridine, can be excluded.

Finally, lacosamide can be isolated from the reaction mixture of step 4 with improved purity by crystallisation in appropriate solvents, such as ethyl acetate.

Experimentally, lacosamide was obtained under the specific conditions of Examples 1 to 4 in a yield of typically 63%-70% (using butyllithium in step 1-A) or 66% to 75% (using PTC in step 1-B). Thus, lacosamide may be obtained by the method of the present invention in a total yield ranging from at least 50% up to 90%, preferably from at least 60% up to 80%. If an organo metal compound is employed the total yield of lacosamide may be more preferably in the range of at least 60% up to 70%, most preferably in the range of at least 63% up to 70%. If a PTC is employed, the total yield of lacosamide may be more preferably in the range of at least 60% up to 75%, most preferably at least 66% up to 75%.

The formation of a compound of formula II from a compound of formula I is comprised by the method of lacosamide synthesis as described above. Subject of the present invention is thus a method for production of a compound of formula (II) from a compound of formula (I) by O-methylation as described above essentially in the absence of methyl ester formation or significant racemisation.

D-serine derivatives or L-serine derivatives or mixtures of D- and L-serine derivatives in any ratio may be used in the method of the present invention.

Due to the fact that during O-methylation of the alcoholic OH-group of D- or/and L-serine derivatives in the method of the present invention, there is essentially no methyl ester formation and no significant racemisation of the product, the method of the present invention for production of a compound of formula (II) or/and of lacosamide leads to an improved yield and an improved enantiomeric purity of the product.

The invention also relates to important intermediates of the current process.

The most important intermediate (R)-2-N-Boc-amino-3-methoxypropanoic acid (C-936) results from the improved O-methylation step according to the present invention (see FIG. 1). The compound can be easily isolated from the reaction mixture as the free acid or by forming a salt, such as e.g. a cyclohexylammonium salt. Suitable C-936 salts are also regarded to be part of the invention.

Also, (R)—N-benzyl-2-N-Boc-amino-3-methoxypropionamide (C-937) which results from the benzyl amide formation (step 2 of FIG. 1) constitutes a part of the invention.

Another aspect of the invention relates to the use of C-936 or C-937 or any salt thereof as an adduct or intermediate in a method of producing (R)-2-acetamido-N-benzyl-3-methoxypropionamide (lacosamide).

Yet another aspect of the invention pertains to a method of producing a pharmaceutical formulation by the subsequent steps of (a) producing lacosamide by the method according to the present invention and (b) mixing lacosamide with pharmaceutically acceptable excipients.

Another aspect of the present invention is a method of producing a compound of formula VIII comprising the O-methylation of a compound of formula VII,

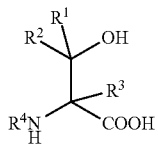

formula VII

I
to produce a compound of formula VIII,

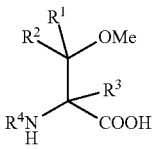

formula VIII wherein $R^4$ is H, an N-protecting group, or/and a group having 0-30 C atoms, and wherein $R^1$, $R^2$, and $R^3$ are independently selected from H and groups having 0-30 C atoms, characterized in that the O-methylation in being carried out in a one-step reaction and wherein the compound of formula VIII is obtained in the same configuration as the compound VII, of at least 88%, preferably of at least 90%, more preferably of at least 95%, 96%, 97%, 98% or 99% enantiomeric purity.

Preferably, $R^1$, $R^2$, and $R^3$ are independently hydrogen, —OH, —SH, —NH$_2$, —NO$_2$, —CN, —COOH, —SOH, —SO$_2$H, —SO$_3$H, halogen, —OR$^{10}$, —SR$^{10}$, —NR$^{10}$R$^{11}$, —SOR$^{10}$, —SO$_2$R$^{10}$, —SO$_3$R$^{10}$, substituted or unsubstituted alkyl as defined above, substituted or unsubstituted $C_2$-$C_6$-alkenyl, substituted or unsubstituted $C_2$-$C_6$-alkynyl, —(CO)—R$^{10}$, —(CO)—O—R$^{10}$, —O—(CO)—R$^{10}$, substituted or unsubstituted aryl as defined above, substituted or unsubstituted $C_3$-$C_{13}$— hetaryl having 1-3 heteroatoms independently selected from N, S, O, substituted or unsubstituted aralkyl as defined above, substituted or unsubstituted $C_7$-$C_{15}$-alkaryl, substituted or unsubstituted $C_4$-$C_{14}$-hetaralkyl having 1-3 heteroatoms independently selected from N, S, O; substituted or unsubstituted $C_4$-$C_{14}$-alkhetaryl having 1-3 heteroatoms independently selected from N, S, O; or substituted or unsubstituted $C_3$-$C_{12}$-cycloalkyl having 0-3 heteroatoms independently selected from N, S, O.

It is more preferred that $R^1$ is H, $R^2$ is H or/and $R^3$ is H. It is most preferred that $R^1$ is H, $R^2$ is H and $R^3$ is H.

Preferably, $R^4$ is selected from $R^1$ and N-protecting groups. More preferably, $R^4$ is the N-protecting group Rx as described above.

Even more preferred is $R^1$ being H, $R^2$ being H, $R^3$ being H and $R^4$ being Rx as described above.

In the substituents $R^4$, $R^1$, $R^2$, $R^3$, the groups $R^{10}$ and $R^{11}$ are independently hydrogen, substituted or unsubstituted alkyl as defined above, substituted or unsubstituted $C_2$-$C_6$-alkenyl, substituted or unsubstituted $C_2$-$C_6$-alkynyl, substituted or unsubstituted aryl as defined above, substituted or unsubstituted $C_3$-$C_{13}$-hetaryl having 1-3 heteroatoms independently selected from N, S, O, substituted or unsubstituted aralkyl as defined above, substituted or unsubstituted $C_7$-$C_{15}$-alkaryl, substituted or unsubstituted $C_4$-$C_{14}$-hetaralkyl having 1-3 heteroatoms independently selected from N, S, O; substituted or unsubstituted $C_4$-$C_{14}$-alkhetaryl having 1-3 heteroatoms independently selected from N, S, O; or substituted or unsubstituted $C_3$-$C_{12}$-cycloalkyl having 0-3 heteroatoms independently selected from N, S, O.

Substitution in the groups $R^4$, $R^1$, $R^2$, $R^3$, $R^{10}$ and $R^{11}$ refers to substitution by one or more substituents as defined above, e.g. by hydroxy, carboxy, halogen, nitro, $C_1$-$C_6$ alkyl, $C_1$-$C_6$ alkoxy, amino, etc.

"The same configuration" of the compound VIII with reference to compound VII means that essentially no racemisation takes place, or compound VIII is obtained in the same configuration as compound VII with an enantiomeric purity as defined above. If compound VII is in the R configuration, compound VIII is also in the R configuration. If compound VII is in the S configuration, compound VIII is also in the S configuration.

It is preferred that compound VII is in the R configuration.

The parameter of enantiomeric purity can be applied mutatis mutandis to enantiomer mixtures. If compound VII is a mixture of the R and S configuration, compound VIII is essentially the same mixture of the R and S configuration, i.e. the ratio of the R and S configuration remains essentially unaltered, or an enantiomeric ratio as follows is obtained. The obtained enantiomeric ratio of compound VIII may be at least 88%, preferably at least 90%, more preferably in at least 95, 96, 97, 98 or 99% of the enantiomeric ratio of compound VII.

"One-step reaction" has the same meaning as discussed above.

The reaction schema of compound VII to compound VIII is a generalization of the O-methylation of the present invention of the compound of formula I to produce a compound of formula II as described above. If the compound VII is in the R configuration, $R^1$ is H, $R^2$ is H, $R^3$ is H and $R^4$ is Rx, the compound VIII corresponds to the compound of formula II and may be used for the production of lacosamide, e.g. by the reaction steps as described above. Starting from the compound II or VII, lacosamide may be produced by any suitable method to introduce the N-benzylamide group and the N-acetyl group. Therefore, in a particular preferred embodiment, the compound VII is in the R configuration and $R^4$ is Rx. It is most preferred that $R^4$ is Rx, $R^1$ is H, $R^2$ is H, and $R^3$ is H and the compound VII is in the R configuration.

The inventive O-methylation of compound VII can be achieved by adding to a compound of formula VII a methylation agent in the presence of an organo metal compound, in particular an organo lithium compound, as defined above. Suitable methylation agents are defined above. In an alternative route, the selective O-methylation of the alcoholic group may be performed by phase transfer catalysis as defined above.

Specific embodiments of the O-methylation of the compound of formula VII correspond to the specific embodiments of the production method of lacosamide comprising the O-methylation of the compound of formula I as described above, in particular specific embodiments relating to the phase transfer catalysis, phase transfer catalysts, in particular as defined in formula IV, V, and VI, the phase transfer reaction system and its components, the organo metal compound, reaction conditions during phase transfer catalysis or in the presence of the organo metal compound, further reaction steps and reaction conditions leading to lacosamide including N-benzylamide formation, N-deprotection and N-acetylation, etc.

The yield of the methylation of compound VII by the method of the present invention may be at least 85%, preferably at least 90% when using an organo metal compound. When using PTC, the yield of methylation of compound VII may be at least 85%, preferably at least 90%, even more preferably at least 91%, 92%, 93%, 94%, 95% or 96%.

Due to the fact that during O-methylation of D- or/and L-serine derivatives in the method of the present invention, there is essentially no methyl ester formation and no significant racemisation of the product, the method of the present invention for production of a compound of formula VIII by methylation of a compound of formula VII leads to an improved yield and an improved enantiomeric purity of the product.

The invention is further illustrated by FIG. 1 (comprising alternative steps 1a or 1b) and the following Examples:

Example 1

Production of (R)-2-N-Boc-amino-3-methoxypropanoic acid (C-936) using butyllithium (step 1a)

A solution of N-Boc-D-serine (22 g, 0.107 mol) in dry tetrahydrofuran (352 ml) was cooled to <−10° C. under a nitrogen atmosphere. To this was added via a dry addition funnel 15% w/w n-butyllithium in hexanes (134 ml, 0.216 mol) keeping the temperature <10° C. The resultant slurry was aged for 1 hour at 0-5° C. Dimethyl sulphate (12.1 ml, 0.128 mol) was added keeping the temperature at 0-5° C. and the reaction mixture aged at 0-5° C. for 9 hours. The reaction was quenched by the addition of water (110 ml), basified to pH 10-13 with 30% sodium hydroxide (3 ml) and the tetrahydrofuran/hexane evaporated in vacuo. The residue was washed with toluene (44 ml) and then acidified to a pH of <3.5 with 50% citric acid. The acidified aqueous phase was extracted with methylene chloride (2×91 ml, 1×66 ml) and the combined C936 extracts dried by azeotropic distillation. Yield on evaporation 23.7 g, 100%. HPLC purity 90.0%, Chiral purity 100%.

Example 2

Production of (R)-2-N-Boc-amino-3-methoxypropanoic acid (C-936) using PTC (step 1b)

A suspension of N-Boc-D-serine (22 g, 0.107 mol) and tetrabutylammonium bromide (1.3 g, 0.004 mol) in toluene (110 ml) was cooled to <10° C. To this was added 20% sodium hydroxide (17.6 ml, 0.107 mol) keeping the temperature <10° C. and the resultant mixture was aged for 30 minutes at <10° C. Dimethyl sulphate (40.6 ml, 0.429 mol) and 50% sodium hydroxide (25.4 ml, 0.485 mol) were added keeping the temperature <10° C. and the reaction mixture aged at 10° C. for 1 hour. Water (66 ml) was added to the mixture and the phases separated. The aqueous layer was acidified to a pH of <3.5 with 50% citric acid, extracted with methylene chloride (2×91 ml, 1×66 ml) and the combined C936 extracts dried by azeotropic distillation. (Yield on evaporation 27.5 g, 100%, HPLC purity 96.3%, Chiral purity 98.1%)

Example 3

Steps 2 to 4

(R)—N-benzyl-2-N-Boc-amino-3-methoxypropionamide (C-937) solution (step 2)

The C936 solution prepared as above in example 2 was cooled to <−10° C. and isobutyl chloroformate (14.2 ml, 0.107 mol) at <−5° C. N-methylmorpholine (11.8 ml, 0.17 mol) was added at <−5° C. and the mixture aged for 30 minutes at <−5° C. A solution of benzylamine (12.2 ml, 0.11 mol) in methylene chloride was added at <−5° C. and the mixture warmed to room temperature. After aging for 1 hour the mixture was washed with water (44 ml), 1N HCl (44 ml), 8% sodium bicarbonate (44 ml) and water (44 ml) to yield a C937 solution in methylene chloride.

(R)-2-amino-N-benzyl-3-methoxypropionamide solution (step 3)

To the C937 solution prepared above was added 36% HCl (46.5 ml, 0.541 mol) and the mixture aged for 1 hour. Water (66 ml) was added and the phases separated. The organic phase was extracted with water (22 ml) and the aqueous layers combined. The aqueous was basified to pH 10-12 with 30% sodium hydroxide at <35° C. and sodium chloride (8.8 g) added. The aqueous layer was extracted with methylene chloride (2×110 ml) and the combined organic layers washed with water (44 ml) yielding a methylene chloride solution of (R)-2-amino-N-benzyl-3-methoxypropionamide.
Lacosamide (step 4)
The (R)-2-amino-N-benzyl-3-methoxypropionamide solution prepared above was cooled to <5° C. and acetic anhydride (10 ml, 0.106 mol) added at <15° C. The reaction mixture is warmed to room temperature over 30 minutes and aged for a further 30 minutes. The mixture is then washed with water (44 ml), 8% sodium bicarbonate (44 ml) and water (44 ml). The methylene chloride was exchanged for ethyl acetate by distillation and the solution distilled to a volume of 115 ml. The product was crystallised by cooling the solution to 0-5° C. and the pure Lacosamide isolated by filtration (18.7 g, 69.8%) HPLC purity 99.98%, Chiral purity 99.8% ee.

Example 4

Isolation of (R)-2-N-Boc-amino-3-methoxypropanoic acid (C-936)

The (R)-2-N-Boc-amino-3-methoxypropanoic acid (C-936) solution prepared in example 1 was evaporated in vacuo yielding (R)-2-N-Boc-amino-3-methoxypropanoic acid (C-936) as a waxy solid (23.7 g, 100%). HPLC purity 90.0%. Elemental analysis Calculated for $C_9H_{17}NO_5$ 49.31% C, 7.82% H, 6.39% N. Found 49.12% C, 7.72% H, 8.97% N.

Example 5

Isolation of (R)—N-benzyl-2-N-Boc-amino-3-methoxypropionamide (C-937)

The (R)—N-benzyl-2-N-Boc-amino-3-methoxypropionamide (C-937) solution prepared in example 3 above was evaporated in vacuo yielding crude C937 as an oily solid. The crude solid (2 g) was dissolved in 10% chloroform in hexane (30 ml) at 60° C., cooled to room temperature and left stand for 1 hour at this temperature. The resulting solids were isolated by filtration yielding crude C937 (1.1 g). This crude solid was further recrystallised twice in 10 volumes of 10% chloroform in hexane to yield (R)—N-benzyl-2-N-Boc-amino-3-methoxypropionamide (C-937) as a white crystalline solid (0.28 g, 14%). HPLC purity 97.3%. Elemental analysis Calculated for $C_{16}H_{24}N_2O_5$ 62.32% C, 7.84% H, 9.08% N. Found 62.19% C, 7.79% H, 9.04% N.

What is claimed is:
1. A method of producing (R)-2-acetamido-N-benzyl-3-methoxypropionamide (lacosamide) comprising methylating a compound of formula I

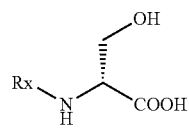

formula I to produce a compound of formula II

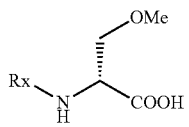

formula II wherein Rx is an N-protecting group,
wherein the methylation is carried out in a one-step reaction by adding a methylation agent and an organo lithium compound to the compound of formula I and wherein the compound of formula II is obtained as an R-enantiomer of at least 88% enantiomeric purity.

2. The method according to claim 1, wherein the methylation agent used with the organo lithium compound is dimethylsulfate.

3. The method according to claim 1, wherein the organo lithium compound is butyl lithium.

4. The method according to claim 1, wherein the methylation in the presence of an organo lithium compound takes place at a temperature of 0-10° C. for at least 5 hours.

5. The method according to claim 1, further comprising reacting the compound II with benzylamine to produce a compound of formula III,

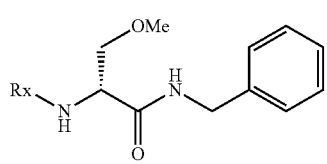

formula III and replacing the protecting group Rx with methyl carbonyl to produce (R)-2-acetamido-N-benzyl-3-methoxypropionamide (lacosamide).

6. The method according to claim 5, wherein the reaction of the compound of formula II with benzylamine takes place in the presence of an activator of the carboxyl group and a base.

7. The method according to claim 6, wherein the base is 4-methylmorpholine, triethylamine, disopropylethalamine, 1,8-diazabycyclo [5.4.0]undec-7-ene or potassium bicarbonate and the activator of the carboxyl group is an alkyl chloroformate or a carbodiimide.

8. The method according to claim 5, wherein the N-protecting group Rx is replaced by methyl carbonyl by successively
(a) cleaving off the protecting group Rx from the compound of formula III by the addition of (i) a mineralic acid or (ii) $H_2$/Pd—C to yield (R)-2-amino-N-benzyl-3-methoxypropionamide and then
(b) adding the methyl carbonyl group to (R)-2-amino-N-benzyl-3-methoxypropionamide by the reaction of (R)-2-amino-N-benzyl-3-methoxypropionamide with acetic anhydride.

9. The method according to claim 8, wherein step (b) is performed in the absence of pyridine.

10. The method according to claim 1, wherein lacosamide is isolated from the final reaction mix by crystallization.

11. The method according to claim 1, wherein the N—protecting group is t-butoxycarbonyl (Boc).

12. A method of producing a pharmaceutical formulation comprising lacosamide by the subsequent steps of
(a) producing lacosamide by the method of claim 1; and
(b) mixing the lacosamide with pharmaceutically acceptable excipients.

13. A method of producing a compound of formula VIII comprising methylating a compound of formula VII,

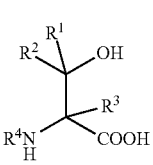

formula VII to produce a compound of formula VIII,

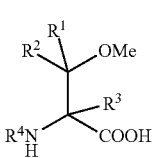

formula VIII wherein $R^4$ is H, an N-protecting group or/and a group having 0-30 C atoms, and wherein $R^1$, $R^2$ and $R^3$ are independently selected from H and groups having 0-30 C atoms,
wherein the methylation is carried out in a one-step reaction by adding a methylation agent and an organo lithium compound to the compound of formula VII wherein the compound of formula VIII is obtained in the same configuration as the compound VII and in at least 88% enantiomeric purity.

14. The method of claim 13, wherein $R^1$ is H, $R^2$ is H, $R^3$ is H and $R^4$ is an N-protecting group.

15. The method of claim 13, wherein the compound VII is in the R-configuration.

* * * * *